United States Patent
Stahmann et al.

(10) Patent No.: US 9,026,221 B2
(45) Date of Patent: May 5, 2015

(54) METHOD AND APPARATUS FOR DETECTION OF LEAD REVERSAL

(71) Applicant: Cardiac Pacemakers, Inc., St. Paul, MN (US)

(72) Inventors: Jeffrey E. Stahmann, Ramsey, MN (US); Mitchell D. Lanz, Maple Grove, MN (US); Eric K. Enrooth, Lino Lakes, MN (US); Jonathan H. Kelly, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/924,011

(22) Filed: Jun. 21, 2013

(65) Prior Publication Data
US 2014/0005749 A1    Jan. 2, 2014

Related U.S. Application Data

(60) Provisional application No. 61/666,369, filed on Jun. 29, 2012.

(51) Int. Cl.
*A61N 1/37*       (2006.01)
*A61N 1/39*       (2006.01)
*A61N 1/375*      (2006.01)

(52) U.S. Cl.
CPC ............... *A61N 1/37* (2013.01); *A61N 1/3706* (2013.01); *A61N 1/3925* (2013.01); *A61N 1/3752* (2013.01)

(58) Field of Classification Search
CPC ..... A61N 1/37; A61N 1/3706; A61N 1/3752; A61N 1/3925
USPC ........................................ 607/27, 28
See application file for complete search history.

(56) References Cited

U.S. PATENT DOCUMENTS

| 7,335,161 | B2 | 2/2008 | Von Arx et al. |
| 7,376,463 | B2 | 5/2008 | Salo et al. |
| 7,440,803 | B2 | 10/2008 | Ni et al. |
| 7,606,619 | B2 * | 10/2009 | Scheiner ..................... 607/27 |
| 7,670,298 | B2 | 3/2010 | Carlson et al. |
| 2010/0114210 | A1 * | 5/2010 | Donofrio et al. ............. 607/5 |

* cited by examiner

*Primary Examiner* — George Evanisko
(74) *Attorney, Agent, or Firm* — Faegre Baker Daniels LLP

(57) ABSTRACT

A medical system including an implantable medical device having at least first and second bores, the first bore configured to receive a first lead, the first lead configured to deliver a first therapy, the second bore configured to receive a second lead, the second lead configured to deliver a second therapy, and a lead reversal detection circuit connected to the at least first and second bores, for detecting insertion of the first or second leads into the wrong bore.

20 Claims, 5 Drawing Sheets

METHOD AND APPARATUS FOR DETECTION OF LEAD REVERSAL

CROSS-REFERENCE TO RELATED APPLICATION

This application claims priority to U.S. Provisional Application No. 61/666,369, filed Jun. 29, 2012, which is herein incorporated by reference in its entirety.

TECHNICAL FIELD

The disclosure relates to implantable medical devices and, more particularly, to implantable medical devices that accept a plurality of different types of leads.

BACKGROUND

Implantable medical devices are often equipped to deliver more than one type of therapy. For example, an implantable pulse generator (IPG) can deliver multiple types of therapy to the heart. A pacing therapy may be appropriate to address bradycardia or slow a stable but rapid heart rhythm. A pacing therapy typically comprises one or more low energy pulses that capture cardiac tissue and set off a depolarization wave. Another type of cardiac therapy is defibrillation therapy. Defibrillation therapy typically comprises a high energy shock that interrupts a rapid and unstable arrhythmia (e.g., fibrillation) in an attempt to reset the heart to a normal cardiac rhythm. The energy level of a pacing pulse is considerably lower than the high energy shock of defibrillation therapy, and as such a pacing therapy can be classified as a low voltage (LV) therapy and defibrillation therapy can be classified as a high voltage (HV) therapy. For example, the energy of a pacing pulse is typically between approximately 5 and 100 microjoules while the energy of a defibrillation shock is typically between approximately 5 and 40 joules. Different leads, which are used to convey therapeutic electrical energy from the IPG to the heart, can be configured in different ways to deliver respective LV and HV therapies. For example, one type of quadripolar lead may have four LV electrodes (LLLL) while another type of quadripolar lead may have two LV electrodes and two HV electrodes (LLHH).

An IPG typically includes bores (e.g., in a header) into which leads can be inserted to mechanically and electrically connect the leads to the IPG. The bores may be dimensioned similarly (e.g., per ISO 27186:2010), such that different types of leads can be placed in different bores of an IPG, even though each bore may be intended to be used with only a particular type of lead (e.g., by having particular channels routed to the bore). In some cases, the bores and leads may not be dimensioned to allow complete insertion of one type of lead (e.g., a LV lead) into a particular bore (e.g., a HV bore). Even so, electrical contact may occur on some or all of the electrodes of a lead if inserted into the wrong bore. A lead may be unintentionally inserted into a bore that is dimensioned to at least partially accept the lead but the type of therapy that the IPG is configured to deliver through the bore and the type of therapy that the lead is configured to deliver may not match, which is an example of lead reversal.

Hazards may exist with lead reversal. For example, it may be unlikely that a defibrillation shock therapy can be effectively delivered using a LV lead that only has electrodes designed for the delivery of LV therapy. Also, delivering defibrillation shock therapy using a LV lead could risk burning the tissue surrounding the LV lead's small electrodes because the small electrodes are not designed to transfer such a large amount of energy to tissue. Finally, the implanted system might be permanently damaged by delivering defibrillation shock therapy through a LV lead or by another unintended arrangement.

SUMMARY

In example 1, a medical system, comprising: an implantable medical device having a first bore and a second bore, the first bore configured to receive a first lead, the first lead configured to perform a first function, the second bore configured to receive a second lead, the second lead configured to perform a second function; and a lead reversal detection circuit connected to at least one of the first bore and the second bore, the lead reversal detection circuit configured to detect one or both of insertion of the first lead into the second bore and insertion of the second lead into the first bore, and to generate an indication of lead reversal based on detection of one or both of insertion of the first lead into the second bore and insertion of the second lead into the first bore.

In example 2, the system of example 1, wherein the implantable medical device is configured to deliver a low voltage (LV) therapy through the first bore; and the first function comprises delivery of the LV therapy.

In example 3, the system of either of examples 2 or 3, wherein the implantable medical device is configured to deliver a high voltage (HV) therapy through the second bore; and the second function comprises delivery of the HV therapy.

In example 4, the medical system of any of examples 1-3, wherein the lead reversal detection circuit is configured to detect one or both of partial insertion of the first lead into the second bore and partial insertion of the second lead into the first bore.

In example 5, the medical system of any of examples 1-4, wherein the lead reversal detection circuit is configured to detect insertion of the second lead into the first bore by: performing a first measurement of a parameter through the first bore; and comparing the first measurement to a first threshold or range, the first threshold or range based on a first level of the parameter expected when the first lead is inserted into the first bore.

In example 6, the medical system of example 5, wherein the lead reversal detection circuit is configured to detect insertion of the first lead into the second bore by: performing a second measurement of the parameter through the second bore; and comparing the second measurement to a second threshold or range, the second threshold or range based on a second level of the parameter expected when the second lead is inserted into the second bore.

In example 7, the medical system of example 5, wherein the parameter comprises cardiac wall motion.

In example 8, the medical system of example 5, wherein the parameter comprises impedance.

In example 9, the medical system of example 5, wherein the parameter comprises inappropriate response to stimulation.

In example 10, the medical system of any of examples 1-9, wherein the lead reversal detection circuit is configured to disable one or more therapies based on detection of one or both of insertion of the first lead into the second bore and insertion of the second lead into the first bore.

In example 11, the medical system of any of examples 1-10, further comprising an external device configured to communicate with the implantable medical device, the external device having an interface and being configured to issue an alert with the interface based on the indication of lead reversal.

In example 12, the medical system of any of examples 1-11, wherein the first lead and the second lead are both quadripolar leads.

In example 13, the medical system of any of examples 1-12, wherein the first lead is an IS-4 lead.

In example 14, the medical system of any of examples 1-13, wherein the second lead is a DF-4 lead.

In example 15, a method of detecting lead reversal in an implantable medical device having a first bore and a second bore, the method comprising: performing a first measurement of a parameter, the first measurement performed through the first bore; comparing the first measurement to a first threshold or range, the first threshold or range based on a first level of the parameter expected when a first lead is inserted into the first bore, the comparison performed by a lead reversal detection circuit; and generating an indication of lead reversal based on the comparison of the first measurement to the first threshold or range indicating that a second lead is inserted into the first bore, the indication generated by the lead reversal detection circuit.

In example 16, the method of example 15, further comprising: performing a second measurement of the parameter, the second measurement performed through the second bore; and comparing the second measurement to a second threshold or range, the second threshold or range based on a second level of the parameter expected when the second lead is inserted into the second bore, the comparison performed by the lead reversal detection circuit, wherein generating the indication of lead reversal is further based on the comparison of the second measurement to the second threshold or range indicating that the first lead is inserted into the second bore.

In example 17, the method of either of examples 15 or 16, wherein: the first lead is configured to deliver only LV therapies; and the second lead is configured to deliver a HV therapy.

In example 18, the method of any of examples 15-17, wherein the parameter comprises impedance.

In example 19, the method of any of examples 15-19, further comprising detecting insertion of either of the second lead or the first lead into the first bore, wherein performing the first measurement and comparing the first measurement to the first threshold or range are performed in response to the detection of insertion.

In example 20, a medical system comprising: an implantable medical device having a first bore and a second bore, the first bore configured to receive a first lead, the implantable medical device configured to deliver a LV therapy through the first bore and deliver a HV therapy through the second bore, the first lead having a first plurality of electrodes configured to deliver the LV therapy, the second lead having a second plurality of electrodes configured to deliver the HV therapy; and a lead reversal detection circuit connected to the first bore and the second bore, the lead reversal detection circuit configured to detect a condition of insertion of the first lead into the second bore and insertion of the second lead into the first bore, and to generate an indication of lead reversal based on detection of the condition.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
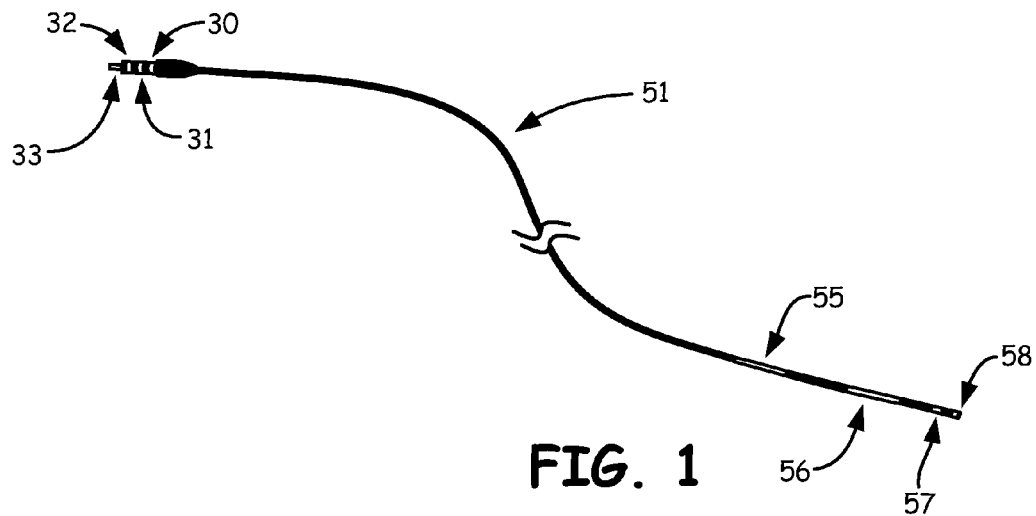
FIG. 1 is a perspective view of the front of an implantable medical device showing the LV IS-4 port and the HV DF-4 port.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Various embodiments of the present disclosure address the problem of lead reversal by detecting inappropriate lead insertion. Various embodiments can include an IPG having a first bore and a second bore, the first bore intended to receive a first lead and the second bore intended to receive a second lead for appropriate therapy delivery. Further bores and leads can be provided, such as a third bore and lead combination. The first and second leads can have different configurations making them respectively suited to deliver different therapies and/or different parts of the same therapies. A lead reversal condition can include the first lead being inserted into the second bore. Another lead reversal condition can concern a swapped arrangement in which the first lead is inserted into the second bore and the second lead is inserted into the first bore. A lead reversal detection circuit can be connected to the first and the second bores or otherwise provided, the lead reversal detection circuit configured to detect insertion of the first lead into the second bore and/or insertion of the second lead into the first bore and generate an indication if lead reversal is detected. The IPG and/or other device can issue an alert warning of the lead reversal condition. Further embodiments are discussed herein.

The configuration of a lead can be customized based on the therapy it is intended to deliver, sensing capabilities, the tissue targeted for stimulation and/or sensing, and/or the implant location of the lead (e.g., the particular cardiac chambers). FIG. 1 shows a perspective view of a HV lead 51 having IPG-to-lead electrodes 30-33 and tissue electrodes 55-58. The IPG-to-lead electrodes 30-33 are located on the proximal end of the HV lead 51 and are configured to make respective electrical connections with different channels of an IPG when inserted into a bore. The tissue electrodes 55-58 are located on the distal end of the HV lead 51 and are configured to deliver electrical stimulation to tissue and/or sense bioelectrical signals from tissue. The tissue electrodes 55-57 may contact tissue of the patient when implanted. Tissue electrode 58 can be a tip electrode. In some cases, a conductive helix may be provided as a tissue electrode on the distal end of the HV lead 51. A helix can be configured to penetrate tissue and deliver electrical stimulation to the tissue. Tissue electrode 57 can be a ring electrode. Ring electrodes are configured to deliver pacing pulses. For example, the exposed surface area of a ring electrode can be relatively small, making the ring electrode well suited for delivering targeted low energy pacing pulses.

The tissue electrodes 55 and 56 can be coil electrodes. Specifically, tissue electrode 55 can be a proximal coil and tissue electrode 56 can be a distal coil. Coil electrodes can be configured to deliver high energy shocks to tissue as a defibrillation or cardioversion therapy. Coil electrodes can have a relatively large exposed surface area which makes them suitable for delivering high amounts of energy. The exposed surface area of a coil electrode can be considerably larger than the exposed surface area of a ring electrode or helix electrode, for example. The arrangement of two ring electrodes distally (suitable for low voltage therapy) and two coils proximally (suitable for high voltage therapy) and can be referred to as a LLHH arrangement.

Coil electrodes are also suitable for delivering lower energy pacing pulses. Four conductors (not illustrated) can extend within the body of the HV lead 51 to electrically connect the IPG-to-lead electrodes 30-33 to the tissue electrodes 55-58, respectively. As such, in some embodiments, each tissue electrode is connected to a single IPG-to-lead electrode. In some variations of the HV lead 51, fewer electrodes can be provided. For example, the HV lead 51 may not include one or more of the IPG-to-lead electrodes 30-33 and/or one or more of the tissue electrodes 55-58. In a variation of the HV lead 51, tissue electrode 57 can be absent. In such an embodiment, the IPG-to-lead electrode 32 can be connected to tissue electrode 56 and tissue electrode 56 can be used to deliver both pacing pulses and shock therapy. In another embodiment of HV lead 51, the tissue electrode 55 can be absent. In such an embodiment, the IPG-to-lead electrode 30 may not be connected to any tissue electrode and shock therapy can be delivered using tissue electrode 56 and the housing of the pulse generator. Other configurations are also possible.

Figure 2:
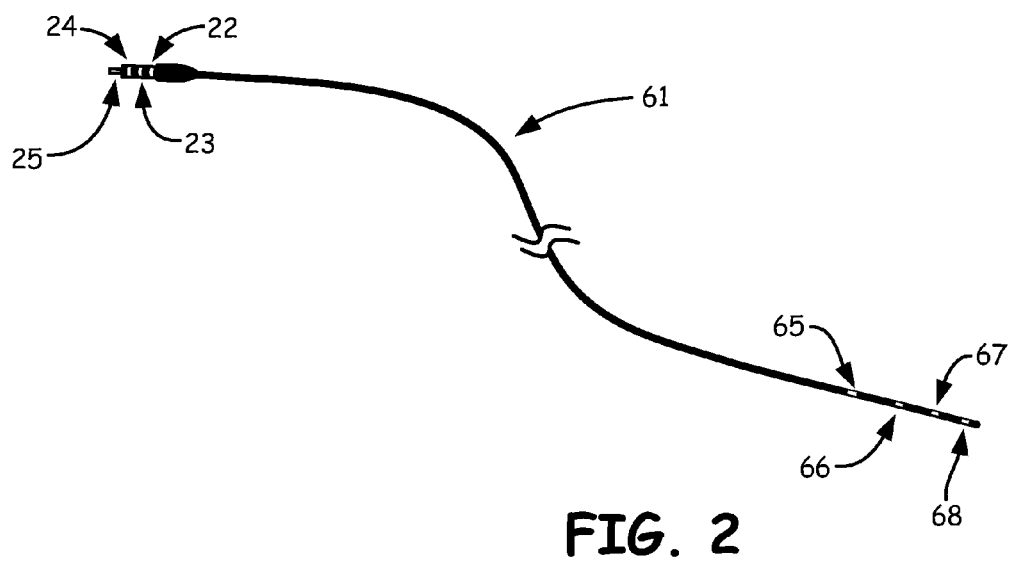
FIG. 2 shows the bores and quadripolar leads in more detail.

FIG. 2 shows a perspective view of a LV lead 61 having IPG-to-lead electrodes 22-25 and tissue electrodes 65-68. The IPG-to-lead electrodes 22-25 are located on the proximal end of the LV lead 61 and are configured to make respective electrical connections with different channels of an IPG when inserted into a bore. The tissue electrodes 65-68 are located on the distal end of the LV lead 61 and are configured to deliver electrical stimulation to tissue and/or sense bioelectrical signals from tissue. The arrangement of four ring electrodes can be referred to as a LLLL arrangement.

Four conductors (not illustrated) can extend within the body of the LV lead 61 to electrically connect the IPG-to-lead electrodes 22-25 to the tissue electrodes 65-68, respectively. In some variations of the LV lead 61, fewer electrodes than those shown in FIG. 2 may be the provided on the LV lead 61. Each of the tissue electrodes 65-68 can be ring electrodes suitable for sensing and/or delivering pacing pulses. It is noted that the LV lead 61 is not suited for delivering a HV therapy, such as defibrillation. Delivery of a HV therapy using the LV lead 61 may be ineffective and/or risk harming the patient and/or equipment.

The HV lead 51 can be an example of a HV lead conforming to the DF-4 standard for a HV quadripolar lead under ISO 27186:2010. Likewise, the LV lead 61 can be an example of a LV lead conforming to the IS-4 standard for a LV quadripolar lead under ISO 27186:2010. While these leads have different electrode configurations suited for delivering different therapies, the proximal ends of the leads are similarly dimensioned to permit at least partial insertion of each lead into the bore intended to receive the other lead. Implantable devices with at least two IS-4/DF-4 quadripolar leads are now commercially available, and more are expected to be commercially released in the future. Therefore, the possibility of a LV lead being inserted into a HV bore, or vice versa can be a problem.

Figure 3:
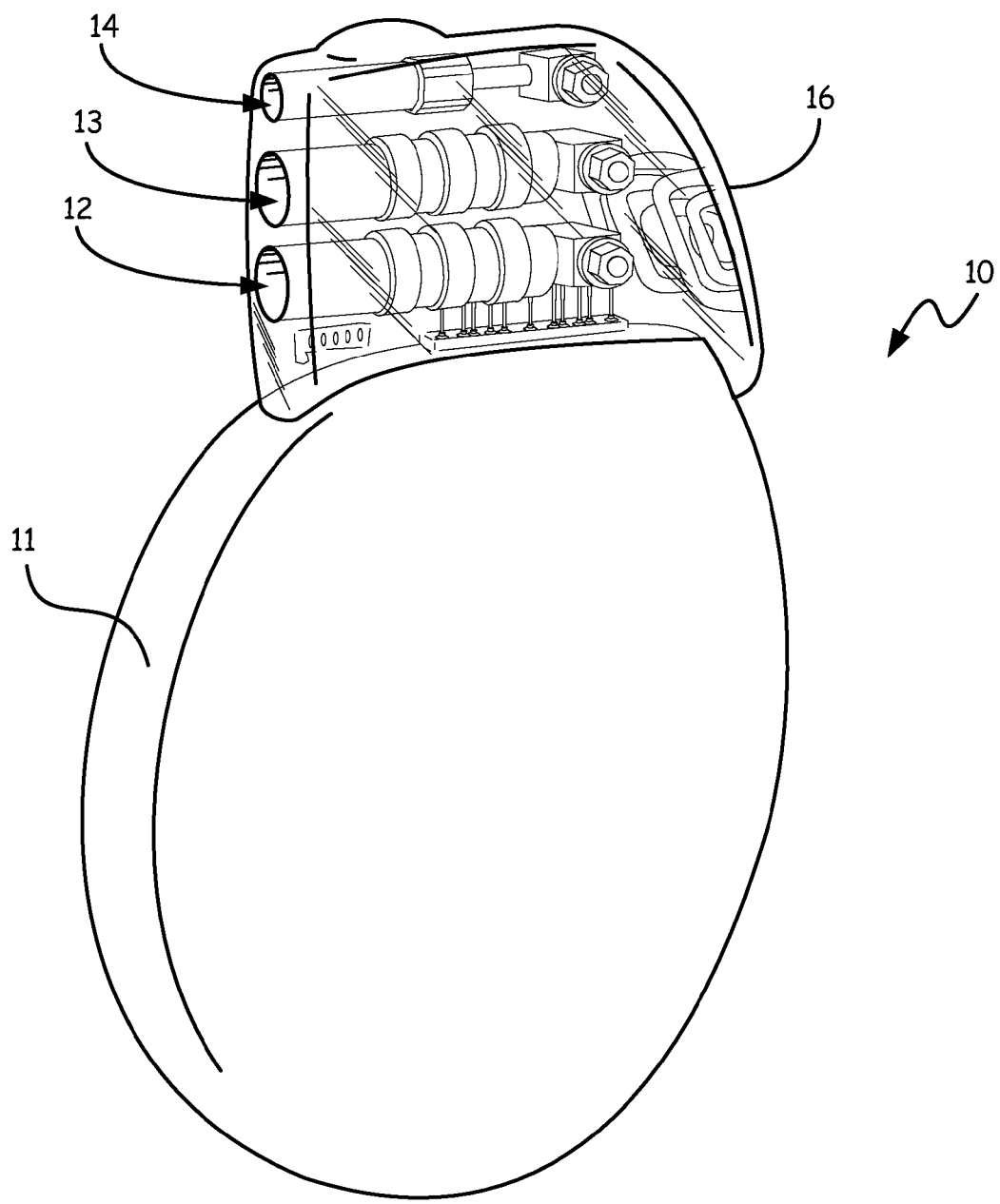
FIG. 3 is a system diagram of a pacemaker configured for biventricular pacing and sensing.

FIG. 3 is a perspective view of an IPG 10. The IPG can be configured to deliver a plurality of different stimulation therapies. For example, the IPG 10 can contain circuitry, as further discussed herein, that is configured to deliver pacing and defibrillation therapies to the heart via leads, such as the HV lead 51 and the LV lead 61 of FIGS. 1-2. The IPG 10 can include a housing 11 and a header 16. The housing 11 can be a metal case. The housing 11 can be electrically connected to circuitry of the IPG 10 such that the housing 11 can function as an electrode (e.g., a return or indifferent electrode). The header 16 can contain bores 12-14. Each of the bores 12-14 can comprise an elongated cavity within the header 16, each bore dimensioned to accept the proximal end of a lead to mechanically and electrically connect the IPG 10 to the lead. Two or more of the bores can have at least some dimensional similarity, such as common diameters and/or lengths. For example, the bores 12 and 13 can be similarly dimensioned and can each partially or fully accept the HV lead 51 and the LV lead 61.

In some embodiments, bore 12 is intended to receive a DF-4 type lead (e.g., HV lead 51), bore 13 is intended to receive an IS-4 type lead (e.g., the LV head 61), and bore 14 is intended to receive an IS-I type lead. Each of the bores 12-14 can be intended to accept a respective type of lead based on the electrical channels that are connected to the bore, to which a lead inserted into the bore would electrically connect, as further discussed in connection with FIG. 4.

Figure 4:
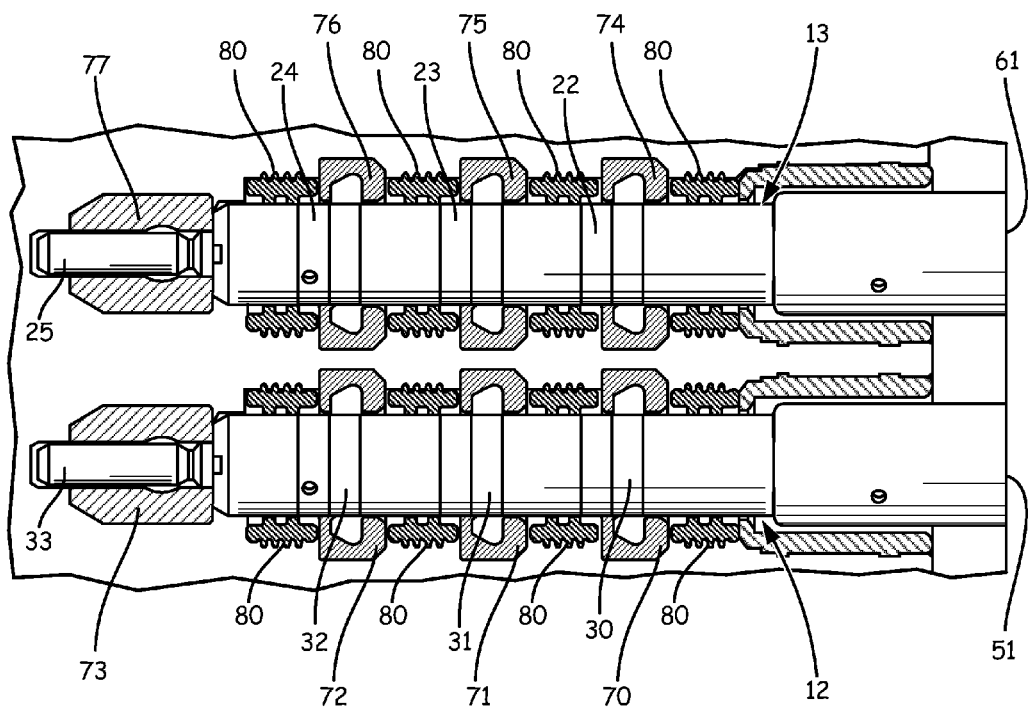
FIG. 4 is a block diagram of the lead reversal impedance test algorithm.

FIG. 4 is a cutaway view of the header 16 of FIG. 3. Specifically, FIG. 4 shows the LV lead 61 inserted into bore 13 and the HV lead 51 inserted into bore 12. Bore 12 includes metal electrical contacts 70-73 which make physical contact with the IPG-to-lead electrodes 30-33, respectively, to establish and maintain electrical connections with channels of the IPG 10. Likewise, bore 13 includes metal electrical contacts 74-77 which make physical contact with the IPG-to-lead electrodes 22-25, respectively, to establish and maintain electrical connections with channels of the IPG 10. Seals 80 can be located between the metal electrical contacts 70-77 to help electrically isolated the channels from each other. Each of the metal electrical contacts 70-77 can electrically connect with a respective channel of a plurality of channels of the IPG 10, as further shown in FIG. 5.

Figure 5:
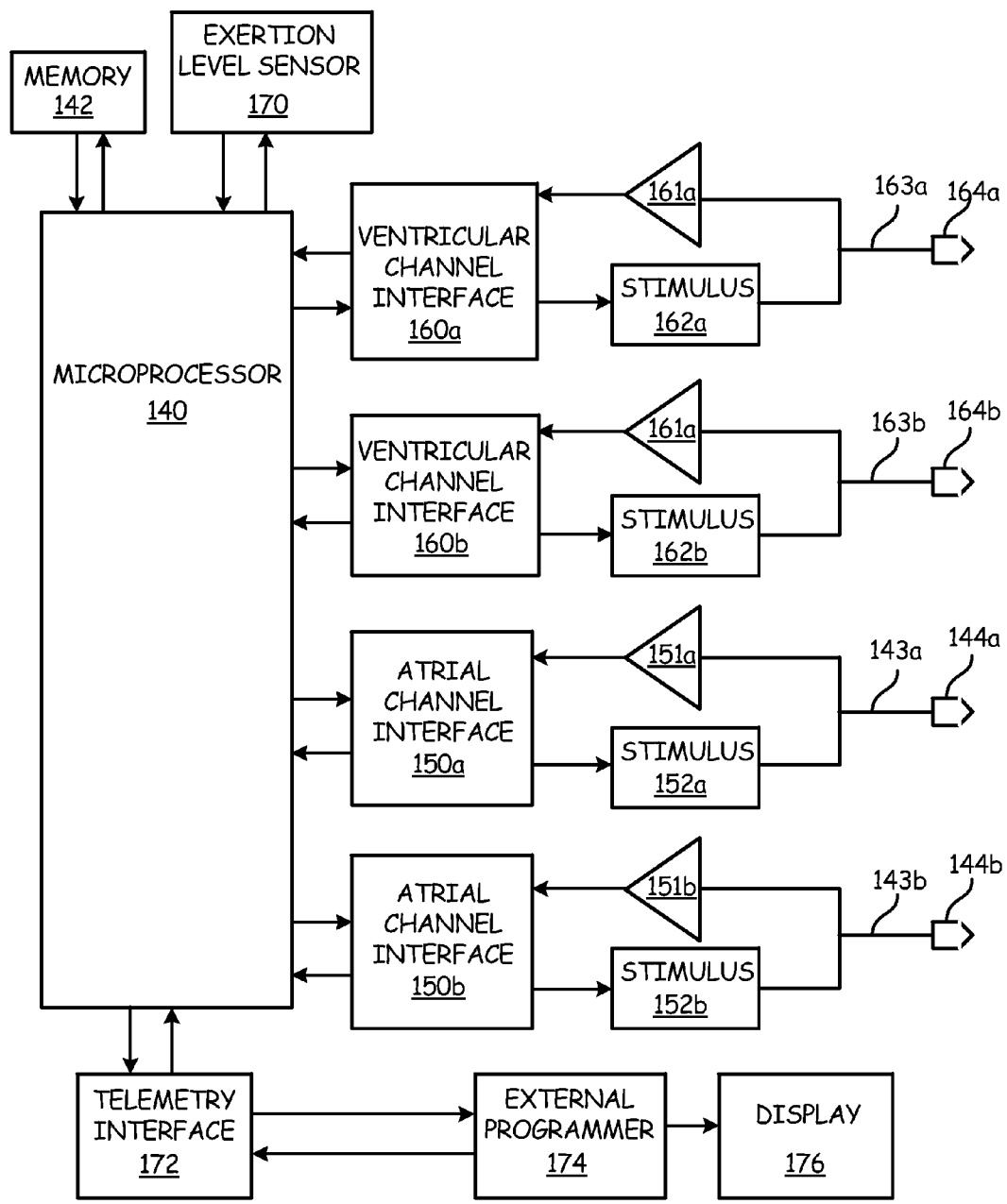
FIG. 5 shows the IPG-to-lead electrodes and tissue electrodes for a DF-4 high voltage lead.

FIG. 5 shows a system diagram of circuitry which can be contained within the IPG 10. The circuitry can route electrical signals through the bores 12-14 to respective leads. The circuitry can be control circuitry for performing the functions referenced herein, such as sensing signals, delivering therapy, and detecting lead reversal, among other functions. The controller 140 can be a microprocessor. The controller 140 can communicate with memory 142 via a bidirectional data bus. The memory 142 can comprise a ROM (read-only memory), a RAM (random-access memory), and/or memory configuration for data and program storage. Atrial sensing and pacing channels can include electrodes 144A-B, leads 143A-B, sensing amplifiers 151A-B, pulse generators 152A-B, and atrial channel interfaces 150A-B. The atrial channel interfaces 150A-B can communicate bidirectionally with controller 140. The schematic representation of electrodes 144A-B and leads 143A-B can correspond to any of the electrodes referenced herein (e.g., the electrodes of FIGS. 1-2). In FIG. 5, "A" designates one ventricular or atrial channel and "B" designates the channel for the contralateral chamber. Two atrial channels are shown in FIG. 5, however a greater or less number of atrial channels can be used.

The circuitry of FIG. 5 can further include ventricular sensing and pacing channels comprising electrodes 164A-B, leads 163A-B, sensing amplifiers 161A-B, pulse generators 162A-B, and ventricular channel interfaces 160A-B. The schematic representation of electrodes 164A-B and leads 163A-B can correspond to any of the electrodes referenced herein (e.g., of FIGS. 1-2). A single electrode can be used for sensing and pacing in each channel in a unipolar configuration. Other embodiments may employ two electrodes for bipolar stimulation and/or sensing. The channel interfaces 160A-B and 150A-B can include analog-to-digital converters for digitizing analog signal inputs from the sensing amplifiers. The channel interfaces 160A-B and 150A-B can include registers which can be written to by the microprocessor in order to adjust an output parameter of stimulation (e.g., pulse amplitude) and/or adjust a sensing parameter for the sensing amplifiers (e.g., gain values). An exertion level sensor 170 (e.g., an accelerometer or a minute ventilation sensor) can be provided to adapt the pacing rate in accordance with changes in the patient's physical activity. A telemetry interface 172 is also provided for communicating with an external programmer 174 which has an associated display 176. An implantable medical device incorporating aspects of the present disclosure may possess some or all of the components in FIG. 5 or otherwise referenced herein. The circuitry of an implantable medical device can be programmable so as to operate in a number of different modes, for example.

The controller 140 can control the overall operation of the IMD 10 in accordance with programmed instructions stored in memory, for example. The controller 140 may be, for example, a microprocessor. The controller 140 controls the delivery of paces via the pacing channels, interprets sense signals from the sensing channels, implements timers for defining escape intervals and sensory refractory periods, performs the pace counting functions, and/or performs other functions. It should be appreciated, however, that these functions could also be performed by custom logic circuitry either in addition to or instead of a programmed microprocessor, such as dedicated gate arrays or other hardware. A shock therapy unit and a shock lead interface can be included amongst the circuitry of FIG. 5. The shock therapy unit can be connected to a shock lead interface and can be controlled by controller 140. In some embodiments, a lead impedance measurement unit is included in the implantable system of FIG. 3. The lead impedance measurement unit is connected to the lead interface circuits and is controlled by controller 140.

The circuitry of FIG. 5 can comprise a lead reversal detection circuit. For example, in accordance with the lead reversal detection techniques referenced herein, one or more signals routed through any of the channel interfaces 150A-B and 160A-B can have a parameter of the signals measured by the channel interfaces 150A-B and 160A-B (e.g., as part of the analog-to-digital conversion of the signals). The parameter can relate to a characteristic of the lead to which the channel is routed, such as impedance of the lead. The parameter can be compared to a threshold or range by the controller 140, the threshold or range stored in memory 142. Based on the comparison, the controller 140 can detect whether the leads are inserted into the appropriate bores or whether the leads are in a reversed arrangement.

Figure 6:
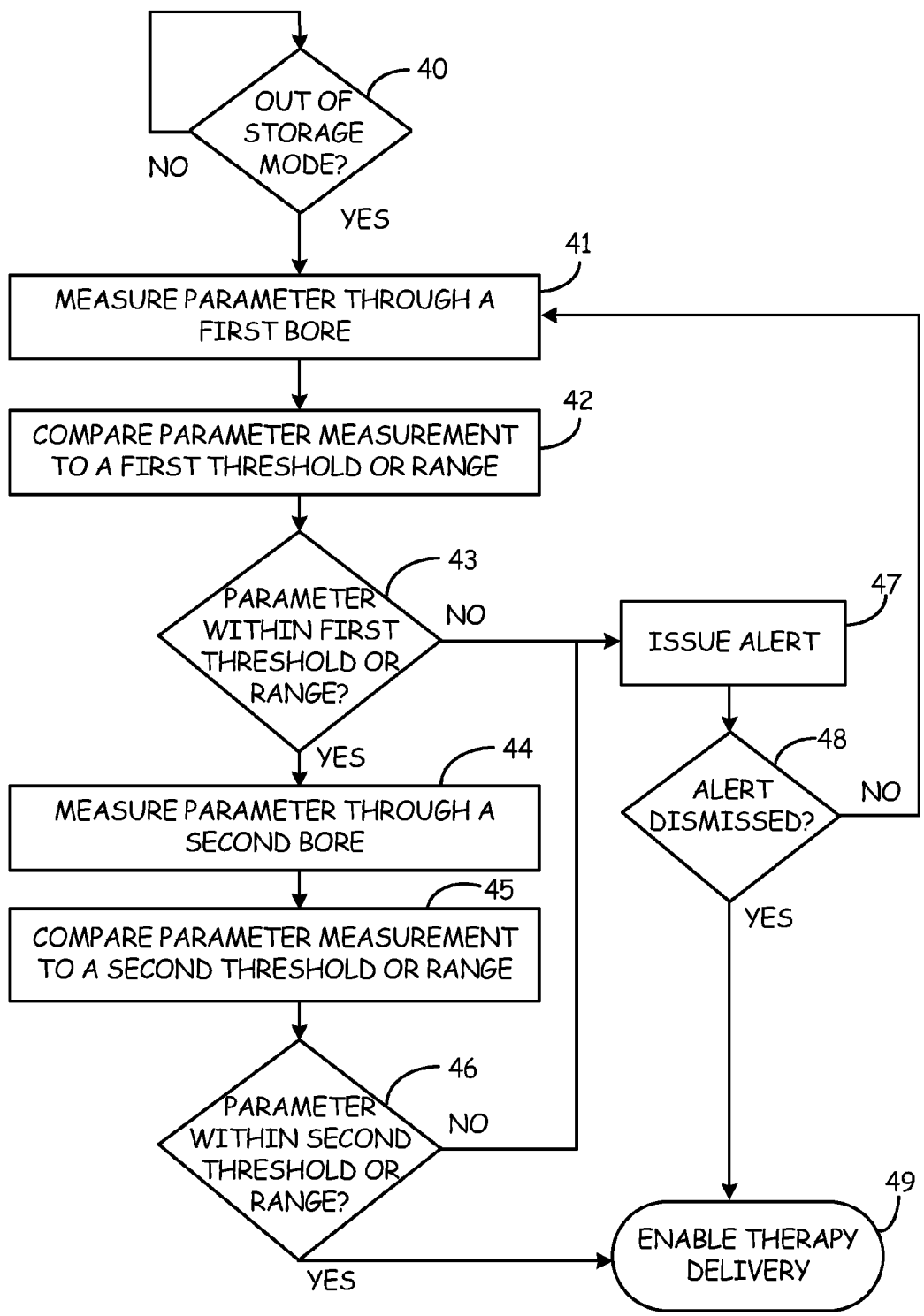
FIG. 6 shows the IPG-to-lead electrodes and tissue electrodes for a IS-4 low voltage lead.

FIG. 6 is a flow chart of an embodiment of a lead reversal detection algorithm which the circuitry of FIG. 5 can be configured to implement. At 40, the program checks whether the device is out of a storage mode. The exiting of the storage mode may be assessed by detection of removal from packaging, handling (e.g., device becomes warm or movement is sensed via an accelerometer), and/or by reception of a wake-up command (e.g., from a programmer). In some cases, the subsequent steps of the flowchart are initiated based on detection of lead insertion.

The program further includes measuring 41 a parameter through a first bore. The parameter can be any parameter referenced herein, such as impedance. The measurement 41 through the first bore can include measuring the parameter through one or more channels that route to the first bore. The measurement 41 can then be compared 42 to a first threshold or range. The first threshold or range can be associated with the first bore and further can be associated with the type of lead intended to be inserted into the first more. In some case, the first bore may be intended to receive a HV lead such that the IPG 10 is configured to deliver a HV therapy through the first bore using the HV lead, as such the first threshold or range can represent a level of the parameter expected for a HV lead. If the parameter is below or within the first threshold or range at step 43, then the program can advance to measuring 44 a parameter through the second bore and comparing 45 the measured parameter to a second threshold or range, which can be performed similarly to the previous measurement 41 and comparison 42 steps. In some case, the second bore may be intended for a LV lead such that the IPG 10 is configured to deliver a LV therapy through the second bore using the LV lead, as such the second threshold or range can represent a level of the parameter expected for a LV lead. In cases where different types of leads are expected to be inserted into the first and second bores, then the first threshold or range can be different from the second threshold or range. If the parameter does not exceed the second threshold or is within the range, at check 46, then proper lead insertion can be confirmed. In some embodiments, confirming proper lead insertion can enable therapy delivery 49, wherein one or more therapies cannot be delivered until therapy delivery is enabled 49.

If either of the measurements 41, 44 exceed the first or second thresholds or is outside of the first or second ranges, according to steps 43 or 46, then the program can issue 47 an alert. The alert can take the form of a buzz or vibration of the implanted medical device 10 itself, or a noise, text, light, or text displayed on an external device. In some cases, the alert may be generated by the circuitry of the IPG 10 and transmitted to an external programmer with an interface. In some cases, the alert may indicate whether one or both of the first and second threshold or ranges are breached thereby indicating if the first and second leads are swapped or whether an incorrect type of lead is being used.

In some embodiments, a user is given an opportunity to dismiss 48 the alert. In some embodiments, an alert must be dismissed a plurality of times (e.g., 3) before the program completes the algorithm and enables 49 therapy delivery, wherein the program returns to measuring 41 after each of the dismissals (except for the final dismissal, which advances the program to step 49). In some cases, the program may pause (e.g., 30 seconds) after each dismissal. The dismissal feature can be useful in case a clinician is still inserting the leads and/or is experimenting with some lead arrangements.

Inappropriate lead insertion can be detected in multiple different ways. For example, one or more characteristics of a lead can be measured upon partial and/or full insertion into a bore. A range or threshold level of a characteristic for a particular type of lead can be known (e.g., stored in memory of IPG 10 and/or the external programmer 174), the range or threshold corresponding to a measure of the characteristic of a type of lead intended for the bore. If the measure of the characteristic exceeds the threshold or is outside of the range, then an alert can be generated to indicate inappropriate lead insertion.

Some other techniques for detecting lead reversal are based on the electrodes from different leads having different configurations and performance characteristics to optimize the leads to carry out the respective functions. For example, all of electrodes of a LV lead may be intended to be implanted within the left ventricle. The electrodes of the LV lead (e.g., ring electrodes) can be different than the electrodes a HV lead (e.g., tip electrode, helix electrode, and/or coil electrode) such that the electrodes have different masses and other aspects that influence their electrical characteristics (e.g., by having different impedances). The differences in lead configurations can be exploited as the measured characteristic of the lead to detect inappropriate lead insertion. For example, a LV lead will likely have greater impedance than a HV lead. A threshold or range can be established for the LV bore and a measure of a characteristic of any lead inserted into the LV bore can be compared to the threshold or range to determine whether the measure is within the threshold or range, as expected of a LV lead, or outside of the threshold or range, as expected of a HV lead. Likewise, a threshold or range can be established for the HV bore and a measure of a characteristic of any lead inserted into the HV bore can be compared to the threshold or range to determine whether the measure is within the threshold or range, as expected of a HV lead, or outside of the threshold or range, as expected of a LV lead. A confirmation indicating correct lead insertion or an alarm indicating inappropriate lead insertion can be generated based on the comparison of the measured characteristic to the threshold or range.

In some embodiments, impedance is measured as a characteristic to check for inappropriate lead insertion. In some cases, lead impedance can be measured by applying a pulse from a lead electrode (e.g., any of tissue electrodes 55-58 or 65-68) to a return electrode. The return electrode can be another tissue electrode on the same lead as the tissue electrode used to deliver the pulse (in a bipolar measurement) or the pulse generator housing 11 (in a unipolar measurement), for example. The energy of the current pulse can be well below the capture threshold of cardiac tissue such that the pulse does not influence cardiac activity or is otherwise physiologically unperceivable. The pulse can be, for example, a single biphasic low amplitude short duration pulse. In some embodiments, the current pulse is either a 160 uA (microamperes) (peak to peak) 156 μs (microseconds) pulse or a 640 uA (peak to peak) 39 μs pulse. The pulse voltage is measured between the lead electrode and the return electrode. The lead impedance can be calculated by dividing the measured voltage by the applied current of the pulse.

An impedance range or threshold can be set for each bore. In some embodiments, the same threshold is used for multiple bores while in some other embodiments each bore has a different impedance threshold. The threshold can be different based on whether the bore is intended to receive a HV lead or a LV lead, for example. Because a LV lead may have a higher impedance relative to a HV lead, a measured impedance of a bore intended to receive a HV lead exceeding a threshold can indicate that a LV lead is inserted into the bore while a measured impedance below the threshold can indicate that a HV lead is inserted into the bore. Likewise, a measured impedance of a bore intended to receive a LV lead below a threshold can indicate that a HV lead is inserted into the bore while a measured impedance above the threshold can indicate that a LV lead is inserted into the bore. In some cases, a single impedance threshold is used, wherein measure impedance above the threshold can indicate that a LV lead is inserted while measure impedance below the threshold can indicate that a HV lead is inserted.

In some cases, the impedance measurement (or other measured characteristic) can be performed using channels known to correspond to different types of tissue electrodes on HV and LV leads. For example, impedance can be measured between the 2nd and 3rd tissue electrodes, which would correspond to the tissue electrodes 56 and 57 (e.g., RV ring and RV distal coil) on the HV lead 51 or the tissue electrodes 66 and 67 (e.g., LV2 and LV3) on the LV lead 61. In this case, the impedance measurement would be different between a ring-to-coil measurement on the HV lead 51 and a ring-to-ring measurement on the LV lead 61, the difference in impedance being used to detect appropriate or inappropriate lead insertion. Impedance can additionally or alternatively be measured between the housing 11 and the 4th tissue electrode (e.g., the most proximal electrode), which would correspond to the coil tissue electrode 55 on the HV lead 51 or the ring issue electrode 65 on the LV lead 61.

In some cases, one or more impedance measurements can test the thoracic or cardiac impedance differences between leads intended for right ventricular and left ventricular implantation. For example, an impedance measurement can be performed on an implanted lead to determine whether the lead is implanted in the correct location for which bore it is inserted (and therefore which channels the lead connects). Lead reversal can be detected if an impedance measurement indicates that a lead inserted into a particular bore, which should be implanted in a chamber or location, has an impedance measurement that indicates that the lead is implanted in a different location. In these cases, an impedance value corresponding to the correct lead and the correct implant location can be stored in memory (e.g., as a range or threshold) and associated with a particular bore. If an impedance measurement conducted though the particular bore does not correspond to this stored value (e.g., by exceeding the threshold or being outside of the range), then an alert indicating inappropriate lead insertion can be generated.

Lead impedance can be measured using various circuitry. For example, one or more impedance measuring modules can be provided within the IPG 10. In some embodiments, impedance sensing circuitry can be integrated into the one or more sensing channels, such as being integrated into one or more of the channel interfaces 160A-B and 150A-B. The exertion level sensor 170 or other sensor that tracks respiration (e.g., by being configured to track minute ventilation) or otherwise measures thoracic impedance can be used to detect measure impedance.

In some embodiments, a range of a LV lead could be, for example, 200-3000 ohms. An impedance threshold for the LV can be any value within this range, and in some cases may be 3000 ohms. In some embodiments, a range of a HV lead could be, for example, 20-200 ohms. An impedance threshold for the HV can be any value within or below this range, and in some cases may be 20 ohms.

The lead reversion detection circuit can utilize various characteristics of a lead to identify particular types of leads and assess whether a particular type of lead that is inserted into a particular bore is intended to be inserted into the bore. For example, the ring electrode may be absent in some HV leads (as compared to the HV lead 51 of FIG. 1) but the proximal end of the lead may still have four IPG-to-lead electrodes to fit within standard bores. One of the IPG-to-lead electrodes may therefore be shorted to another one of the IPG-to-lead electrodes (e.g., the middle two IPG-to-lead electrodes). Therefore, such a HV lead may be identified if very low resistance is measured between the shorted IPG-to-lead electrodes. If such a test performed through a bore intended to accept a LV test confirms the presence of a HV lead, then an indication of lead reversal can be generated. In another example, instead of shorting two of the IPG-to-lead electrodes, one of the IPG-to-lead electrodes may be left as an open circuit. In this case, detection of the open circuit on one of the IPG-to-lead electrodes may be used as an indicator of the type of lead, and if the lead is inserted into a bore that is not intended to receive that type of lead, then an indication of lead reversal can be generated.

In some embodiments, inappropriate lead insertion can be detected based on the relative timing of the sensing of cardiac signals and/or event detection. Intracardiac electrocardiograms ("e-grams") can be measured by the IPG 10 in any and all chambers. During ventricular systole, different portions of the ventricles will depolarize at different times, hence the e-grams from different locations in the heart will predictably occur at different times. In most cases, right ventricular tissue will depolarize before left ventricular tissue. This is particularly true in Cardiac Resynchronization Therapy (CRT) patients since these patients typically have bundle branch block prolonging their QRS duration. In many applications of CRT, a HV lead is implanted in the right ventricle and a LV lead is implanted along the left ventricle within the great cardiac vein. In a system with properly inserted leads, the e-gram sensed via the bore intended to receive the HV lead will normally occur before the e-gram sensed via the bore intended to receiver the LV lead. If the leads are reversed, then the e-gram sensed via the bore intended to receive the HV lead will indicate an earlier depolarization than the signal sensed via the bore intended to receive the LV lead in each cardiac cycle. It is noted that using the relative timing of sensed cardiac events to detect lead reversal may be particularly effective in wholly intrinsic (i.e. not paced) beats, however the technique can be used in cases where pacing is present.

In some embodiments, lead reversal can be detected based on the delivery of pacing pulses. In some embodiments, the difference in evoked response e-gram morphology resulting from pacing different regions of the heart or other anatomy may indicate appropriate or inappropriate lead insertion. In some cases of CRT, a quad-polar LV lead is implanted extending through the coronary sinus and into the great cardiac vein such that the LV4 electrode (i.e. most proximal) lies on the left ventricle while the proximal coil electrode (i.e. most proximal) of a quad-polar HV lead resides in the superior vena cava. If these leads are plugged into the incorrect bores, the evoked response e-grams from pacing these electrodes will be different than had the leads been correctly inserted. For example, pacing through the proximal coil electrode on the HV lead will typically result in no evoked response e-gram. As such, when a pulse that is delivered to what is intended to be the LV4 electrode on a LV lead fails to generate an evoked response, then an indication of lead reversal can be generated and/or more testing initiated.

In some embodiments, the difference in pacing voltage thresholds between a LV electrode and a HV electrode can be used to detect lead reversal. More specifically, lead reversal can be checked by performing a capture test using a voltage level likely to result in successful capture if delivered using an appropriate electrode and unlikely to result in successful capture if delivered using an inappropriate electrode. For example, the pacing threshold of cardiac tissue when using a HV proximal coil electrode is typically much higher than when a LV ring electrode is used. In some cases, delivering a pace pulse at 2 volts would typically capture (i.e. cause a contraction) cardiac tissue with a LV electrode but not with the HV distal coil electrode. In a lead reversal test, a pace pulse can be delivered at a particular energy level using a channel associated with a bore intended to receive a LV lead, the pace pulse known to cause capture at the energy level if delivered using a particular type of electrode. If the pulse fails to capture tissue, then an indication of lead reversal can be generated. In some cases, a second test can be performed to further confirm lead reversal, the second test including the delivery of a second pacing pulse at a higher energy level, the second pace pulse known to cause capture at the higher energy level if delivered using a HV electrode. If capture is detected with the second pace pulse but not the first, then an indication of lead reversal can be generated. In another embodiment, detecting lead reversal can include altering the return (i.e. non-pacing site electrode) electrode and measuring the return electrode's effect on pacing capture voltage.

Some techniques for detecting lead reversal while pacing can be based on the depolarization sequence and/or duration. If the depolarization sequence proceeds from LV1 to LV4 (i.e. the depolarization is first sensed using the LV1 electrode, and next is sensed on the LV2 electrode, and is next sensed on the LV3 electrode, and is then sensed on the LV4 electrode) and occurs within a left ventricular time window (e.g., is within 100 milliseconds), then this detection pattern can be an indication that the leads are appropriately inserted. However, if the depolarization sequence does not proceed from LV1 to LV4 and/or exceeds a typical left ventricular depolarization time (e.g., is greater than 100 milliseconds), then the leads are not appropriately inserted and an indication of lead reversal can be generated.

The lead reversal detection circuit can utilize cardiac freewall motion as an indicator of appropriate or inappropriate lead insertion. Specifically, lead reversal can be detected based on the relative timing of the freewall motion associated with different chambers. In some embodiments, monitor freewall motion can be monitored via measuring the impedance across the heart (e.g., as trans-cardiac impedance). U.S. Pat. No. 7,440,803 entitled "Closed Loop Impedance-Based Cardiac Resynchronization Therapy Systems, Devices, and Methods," which is hereby incorporated herein by reference in its entirety, describes measuring cardiac freewall motion. As described in U.S. Pat. No. 7,440,803, due to the impedance differences between blood and tissue, and the relative changes of blood and tissue associated with a beating heart, trans-cardiac impedance can be used to provide a measurement of the cardiac freewall motion. The measurement can be directed, or focused, on different portions (e.g. chambers) of the heart. Left ventricular freewall/chamber motion is normally delayed from right ventricular freewall/chamber motion in intrinsic cardiac cycles. In many applications of CRT, a HV lead is implanted in the right ventricle and a LV lead is implanted along the left ventricle within the great cardiac vein. In a system with properly inserted leads, a contraction of a chamber, as indicated by freewall motion or other mechanical event, can be sensed first via the bore intended to receive the HV lead and then by the bore intended to receive the LV lead. If the leads are reversed, then a contraction sensed via the bore intended to receive the LV lead before a contraction is sensed via bore intended to receive the HV lead will indicate lead reversal.

Lead reversal can be detected in some embodiments by determining whether an improvement in cardiac rhythm and/or hemodynamic performance results from therapy delivery. Improvement in cardiac rhythm and/or hemodynamic performance can indicate proper lead insertion while little improvement, no improvement, or deterioration of cardiac rhythm and/or hemodynamic performance can indicate lead reversal.

In some cases, lead reversal can be detected based on an inappropriate response to a pacing pulse. For example, when a HV lead is implanted in the right ventricle and a LV lead is implanted in the left ventricle (which corresponds to a typical configuration for CRT), then the delivery of CRT will cause a predictable improvement in some hemodynamic parameters (e.g., increases in pulse pressure and perfusion) in most patients. Left ventricular contractility increases during properly applied CRT in many patients. However, if the leads are reversed, then no improvement and a potential worsening of left ventricular contractility may be more likely to occur. Cardiac contractility can be measured by an implanted device by, for example, measurement of a heart sound intensity or other parameter via an accelerometer or by measuring the left ventricular wall motion via impedance. U.S. Pat. No. 7,376,463 entitled, "Therapy control based on the rate of change of intracardiac impedance" which is hereby incorporated herein by reference, describes a system capable of measuring contractility via impedance. U.S. Pat. No. 7,670,298 entitled "Sensing rate of change of pressure in the left ventricle with an implanted device" which is hereby incorporated herein by reference in its entirety, describes a system capable of measuring contractility via the heart sound. An inappropriate response can also be detected via an implanted hemodynamic sensor such as a blood pressure or blood flow sensor. U.S. Pat. No. 7,335,161 entitled, "Techniques for blood pressure measurement by implantable device" which is hereby incorporated herein by reference in its entirety, describes an implantable blood pressure and blood flow sensor. Cardiac rhythm and/or hemodynamic performance thresholds can be set based on any metric referenced herein (e.g., a measure of contractility) to delineate improved cardiac rhythm and/or hemodynamic performance (indicating proper lead insertion) from non-improved or diminished cardiac rhythm and/or hemodynamic performance (indicating lead reversal).

A check for lead reversal can be performed at various times. For example, any lead reversal test referenced herein can be performed periodically at, and/or after, any of: the IPG exits shipping or storage mode, at a first or subsequent interrogation of the IPG by a programmer, upon a prompt from the user that the implant procedure has begun, when lead insertion is detected (via an open circuit test) on any lead bore, when lead insertion is detected for all bores, and/or any other event. In some cases, a lead reversal test may be required before induction of fibrillation by the physician is allowed. In some cases, fibrillation is induced to test the efficacy of the implant setup (e.g., lead position). However, if two or more of the leads are reversed, than it may be helpful to prevent induction of fibrillation until it is confirmed that the leads are inserted into the correct bores.

In some cases, lead reversal detection testing may be initiated only after the implanter has completed the lead insertion portion of the implant procedure, otherwise false alerts may be triggered. In some embodiments, a programming step is required which indicates that the implant procedure is complete or that other actions by the implanter are accomplished. An indication of completion can be wirelessly communicated from the programmer to the IPG. Other programming steps for enabling or triggering lead reversal testing can include tachycardia therapy being turned on, initiation of a Ventricular Fibrillation (VF) induction, initiation of a measurement using the affected leads (e.g. capture threshold, R-wave amplitude, impedance), or other function concerning the leads. In some embodiments, the clinician may be required to dismiss a notification to verify proper lead placement before proceeding with a VF induction procedure. For example, a query on a programmer can be automatically generated prompting the physician to check lead insertion or prompting the physician to initiate a lead reversal test. In some cases, a programmer may not allow dismissal of a warning until a lead reversal check has been performed or other indicator of proper lead insertion has been received (e.g., an e-gram containing normal or otherwise expect patterns). In some sensing tests, electrode use is restricted to only lead electrodes, thereby eliminating the need for the housing of the IPG to be in contact with tissue which may otherwise be required for unipolar e-grams. However, in some other cases, a unipolar e-gram may be used, thereby testing whether the IPG housing is in contact with tissue.

Various steps can be taken if inappropriate lead insertion is detected. In some embodiments, an indication of lead reversal can be generated, which can comprise a graphical indication on a screen of a programmer, an audible alarm, and/or a vibration. In some cases, a graphical indication of the lead insertion status can be provided on a programmer interface with a first color (e.g., green) indicating proper insertion, a second color (e.g., red) indicating improper insertion, and a third color (e.g., white) indicating no insertion being displayed. The IPG 10 may be configured to generate an indication, such as a noise, vibration, and/or a message transmitted wirelessly to an external programmer or another device upon detection of lead reversal. In some embodiments, one or more functions may be disabled upon detection of lead reversal. For example, delivery of HV shock therapy (e.g., defibrillation) may be inhibited upon detection of lead reversal. Preventing delivery of a shock will prevent burn-related injury to the patient and damage to the implanted system. In some cases, one or more therapy delivery functions may be disabled upon detection of lead reversal, such as high energy defibrillation therapy, while the delivery of one or more other therapy functions (e.g., pacing) is still allowed. A disabled therapy or other function may then be re-enabled upon a subsequent lead reversal test indicating proper lead insertion.

In some implementations, common types of leads are implanted in a patient. For example, two IS-4 type leads may be implanted in a patient and plugged into two bores intended to receive IS-4 type leads. While the leads may function similarly, each of the different ports may have channels intended to be used to sense and/or stimulate different targets. For example, one of the bores may be intended to receive an IS-4 type lead that is intended to be used for cardiac pacing and another bore may be intended to receive another IS-4 type lead that is intended to be used for low voltage therapy such as neural stimulation. One or more thresholds or ranges can be associated with each of the bores, each threshold or range associated with an expected measurement parameter level for the intended application of the lead that the bore is intended to receive. For example, an impedance level or range can be associated with the bore intended to receive the lead intended to be implanted within the heart, the impedance level or range based on the level of impedance that may normally be expected from a lead implanted in a heart. If impedance or other measured parameter is below the threshold or within the range, then proper lead insertion can be confirmed, but if the impedance or other measure parameter exceeds the threshold or is outside of the range, then an indication of lead reversal can be generated.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical system, comprising:
an implantable medical device having a first bore and a second bore, the implantable medical device configured to output a low voltage (LV) therapy through the first bore and output a high voltage (HV) therapy through the second bore, the first bore configured to receive a first type of lead, the first type of lead configured to deliver the LV therapy output from the first bore, the second bore configured to receive a second type of lead, the second type of lead configured to deliver the HV therapy output from the second bore; and
a lead reversal detection circuit connected to the first bore and the second bore, the lead reversal detection circuit configured to:
  detect insertion of the first type of lead into the second bore by performing a first measurement of a parameter through the second bore and comparing the first measurement to a first threshold or range, wherein the first threshold or range is based on the second type of lead and the first type of lead is detected to be in the second bore based on whether the first measurement is above or below the first threshold or inside or outside the first range,
  detect insertion of the second type of lead into the first bore by performing a second measurement of the parameter through the first bore and comparing the second measurement to a second threshold or range, wherein the second threshold or range is based on the first type of lead and the second type of lead is detected to be in the first bore based on whether the second measurement is above or below the second threshold or inside or outside the second range, wherein the first threshold or range is different than the second threshold or range, and
  generate an indication of lead reversal indicating that the first type of lead is in the second bore and that the second type of lead is in the first bore based on detection of both of insertion of the first type of lead into the second bore and insertion of the second type of lead into the first bore.

2. The medical system of claim 1, wherein the lead reversal detection circuit is configured to disable output of the HV therapy from the second bore based on the detection of insertion of the first type of lead into the second bore.

3. The medical system of claim 2, wherein the implantable medical device is configured to output the LV therapy from the second bore using the first type of lead to deliver the LV therapy based on detection of insertion of the first type of lead into the second bore.

4. The medical system of claim 1, wherein the lead reversal detection circuit is further configured to detect one or both of partial insertion of the first type of lead into the second bore and partial insertion of the second type of lead into the first bore.

5. The medical system of claim 1, wherein comparing the first measurement to the first threshold or range comprises comparing the first measurement to the first range, and wherein comparing the second measurement to the second threshold or range comprises comparing the second measurement to the second range.

6. The medical system of claim 5, wherein the first range does not overlap with the second range.

7. The medical system of claim 1, wherein the parameter comprises impedance.

8. The medical system of claim 1, wherein the parameter comprises timing of cardiac wall motion.

9. The medical system of claim 1, wherein the parameter comprises inappropriate response to stimulation.

10. The medical system of claim 1, wherein the lead reversal detection circuit is configured to disable one or more therapies based on detection of one or both of insertion of the first type of lead into the second bore and insertion of the second type of lead into the first bore.

11. The medical system of claim 1, comprising an external device configured to communicate with the implantable medical device, the external device having an interface and being configured to issue an alert with the interface based on the indication of lead reversal.

12. The medical system of claim 1, wherein the first bore and the second bore are configured to receive the first type of the lead and the second type of lead as quadripolar leads.

13. The medical system of claim 1, wherein the first bore is configured to receive the first type of lead as an IS-4 lead.

14. The medical system of claim 1, wherein the second bore is configured to receive the second type of lead as a DF-4 lead.

15. A method of detecting lead reversal in an implantable medical device having a first bore configured to receive a first type of lead and a second bore configured to receive a second type of lead the method comprising:
performing a first measurement of a parameter, the first measurement performed through the first bore;
comparing the first measurement to a first threshold or range, the first threshold or range based on a first level of the parameter expected when the first second type of lead is inserted into the first bore, the comparison performed by a lead reversal detection circuit;
performing a second measurement of the parameter, the second measurement performed through the second bore;
comparing the second measurement to a second threshold or range, the second threshold or range based on a second level of the parameter expected when the first type of lead is inserted into the second bore, the comparison performed by the lead reversal detection circuit, wherein the first threshold or range is different than the second threshold or range, and
generating an indication of lead reversal indicating that the first type of lead is in the second bore and that the second type of lead is in the first bore based on both of the comparison of the first measurement to the first threshold or range indicating that the second type of lead is inserted into the first bore and the comparison of the second measurement to the second threshold or range indicating that the first type of lead is inserted into the second bore, the indication generated by the lead reversal detection circuit.

16. The method of claim 15, wherein comparing the first measurement to the first threshold or range comprises comparing the first measurement to the first range, comparing the second measurement to the second threshold or range comprises comparing the second measurement to the second range, and the first range does not overlap with the second range.

17. The method of claim 15, wherein:
the first type of lead is configured to deliver only LV therapies;
the second type of lead is configured to deliver a HV therapy; and the method further includes disabling the implantable medical device from delivering the HV therapy based on the comparison of the second measurement to the second threshold or range indicating that the first type of lead is inserted into the second bore.

18. The method of claim 15, wherein the parameter comprises impedance.

19. The method of claim 15, further comprising detecting insertion of either of the second type of lead or the first type of lead into the first bore, wherein performing the first measurement and comparing the first measurement to the first threshold or range are performed in response to the detection of insertion.

20. A medical system comprising:
a first type of lead;
a second type of lead;
an implantable medical device having a first bore and a second bore, the first bore configured to receive the first type of lead and the second bore configured to receive the second type of lead, the implantable medical device configured to deliver a LV therapy through the first bore and deliver a HV therapy through the second bore, the first type of lead having a first plurality of electrodes configured to deliver the LV therapy, the second type of lead having a second plurality of electrodes configured to deliver the HV therapy; and a lead reversal detection circuit connected to the first bore and the second bore, the lead reversal detection circuit configured to:
perform a first measurement of a parameter through the first bore;
compare the first measurement of the parameter to a first threshold or range, the first threshold or range associated with the second type of lead;
perform a second measurement of the parameter through the second bore;
compare the second measurement of the parameter to a second threshold or range, the second threshold or range associated with the first type of lead;
detect a condition of lead reversal wherein the first type of lead is inserted into the second bore while the second type of lead is inserted into the first bore based on the comparison of the first measurement to the first threshold or range and the comparison of the second measurement to the second threshold or range; and
generate an indication of lead reversal indicating that the first type of lead is in the second bore and that the second type of lead is in the first bore based on detection of the lead reversal condition.

* * * * *